US010306926B2

(12) United States Patent
Borkovec

(10) Patent No.: US 10,306,926 B2
(45) Date of Patent: Jun. 4, 2019

(54) ELECTRONIC SMOKING DEVICE

(71) Applicant: Fontem Holdings 2 B.V., Amsterdam (NL)

(72) Inventor: Vaclav Borkovec, Hamburg (DE)

(73) Assignee: FONTEM HOLDINGS 1 B.V., Amsterdam (NL)

( * ) Notice: Subject to any disclaimer, the term of this patent is extended or adjusted under 35 U.S.C. 154(b) by 406 days.

(21) Appl. No.: 15/070,637

(22) Filed: Mar. 15, 2016

(65) Prior Publication Data

US 2016/0270447 A1 Sep. 22, 2016

(30) Foreign Application Priority Data

Mar. 19, 2015 (EP) .................................... 15159775

(51) Int. Cl.

| | |
|---|---|
| ***A61M 15/06*** | (2006.01) |
| ***H05B 1/02*** | (2006.01) |
| ***H05B 3/00*** | (2006.01) |
| ***H05B 3/42*** | (2006.01) |
| ***A24F 47/00*** | (2006.01) |

(52) U.S. Cl.

CPC ......... *A24F 47/008* (2013.01); *H05B 1/0244* (2013.01); *H05B 3/0014* (2013.01); *H05B 3/42* (2013.01)

(58) Field of Classification Search

None

See application file for complete search history.

(56) References Cited

U.S. PATENT DOCUMENTS

| | | | | |
|---|---|---|---|---|
| 2,846,560 A * | 8/1958 | Jacoby | H01C 7/04 219/505 |
| 4,547,658 A * | 10/1985 | Crowley | H05B 3/342 219/212 |
| 4,742,212 A * | 5/1988 | Ishii | H05B 3/56 174/107 |
| 5,144,962 A * | 9/1992 | Counts | A24F 47/008 128/200.14 |

(Continued)

FOREIGN PATENT DOCUMENTS

| | | |
|---|---|---|
| EP | 0430559 A2 | 6/1991 |
| WO | 2014004648 A1 | 1/2014 |

(Continued)

OTHER PUBLICATIONS

European Patent Office, European search report issued in EP Patent Application No. 15159775.4 (Oct. 26, 2015).

(Continued)

*Primary Examiner* — Thor S Campbell

(74) *Attorney, Agent, or Firm* — Perkins Coie LLP; Kenneth H. Ohriner

(57) ABSTRACT

An atomizer (26) for an electronic smoking device (10) is provided comprising at least a first heating wire (40) and a second heating wire (50). The first and second heating wires (40, 50) are wound together to form a common heating coil (28). Further, the first and second heating wires (40, 50) differ in at least one physical parameter leading to different thermal properties of the heating wires (40, 50). Additionally, an electronic smoking device (10) comprising the atomizer (28) and a cartomizer (700) for an electronic smoking device (10) are provided.

12 Claims, 10 Drawing Sheets

(56) References Cited

U.S. PATENT DOCUMENTS

| | | | | |
|---|---|---|---|---|
| 6,234,167 | B1 * | 5/2001 | Cox | A61M 15/0003 128/200.14 |
| 7,989,740 | B2 * | 8/2011 | Whitney | H05B 6/56 219/212 |
| 9,301,547 | B2 * | 4/2016 | Liu | A24F 47/008 |
| 9,603,386 | B2 * | 3/2017 | Xiang | A24F 47/008 |
| 9,675,114 | B2 * | 6/2017 | Timmermans | A24F 47/008 |
| 9,730,473 | B2 * | 8/2017 | Shinkawa | A24F 47/008 |
| 9,848,644 | B2 * | 12/2017 | Plunkett | A24F 47/008 |
| 9,918,495 | B2 * | 3/2018 | DePiano | A24F 47/008 |
| 2006/0163232 | A1 * | 7/2006 | Hollander | H05B 3/46 219/202 |
| 2013/0026904 | A1 * | 1/2013 | De Santiago | H01K 1/14 313/274 |
| 2013/0315575 | A1 * | 11/2013 | DeSantiago | H01K 1/18 392/407 |
| 2014/0000638 | A1 * | 1/2014 | Sebastian | A24F 47/008 131/328 |
| 2014/0209105 | A1 * | 7/2014 | Sears | F22B 1/28 131/328 |
| 2014/0314397 | A1 | 10/2014 | Alima | |
| 2014/0366898 | A1 * | 12/2014 | Monsees | A24F 47/008 131/329 |
| 2015/0013702 | A1 | 1/2015 | Liu | |
| 2015/0059787 | A1 | 3/2015 | Qiu | |
| 2015/0083147 | A1 * | 3/2015 | Schiff | A24F 47/008 131/329 |
| 2017/0224021 | A1 * | 8/2017 | Xiang | A24F 47/008 |

FOREIGN PATENT DOCUMENTS

| | | | |
|---|---|---|---|
| WO | 2014101119 | A1 | 7/2014 |
| WO | 20140107837 | A1 | 7/2014 |
| WO | 20140160055 | A1 | 10/2014 |

OTHER PUBLICATIONS

Intellectual Property Office, Combined Search and Examination Report issued in GB Patent Application No. GB1508417.1 (Jul. 27, 2015).

Great Brittan, Examination Report, Application No. GB1508417.1, dated Apr. 10, 2017, 5 pp.

“Top 10 Coil Builds”, retrieved online Apr. 7, 2017, from: https://www.youtube.com/watch?v=sEjBPHyrlVU.

“Twisted 28 and 20g coil”, retrieved online Apr. 7, 2017, from: https://www.youtube.com/watch?v=LKjaOxKPMlw.

“Twisted 26g paralleled 2 24g kanthal”, retrieved online Apr. 7, 2017, from: https://www.youtube.com/watch?v=Dco-rtcqQWw.

“Parallel spiral wire nichrome dry fire vid”, retrieved online Apr. 7, 2017, from: https://www.youtube.com/watch?v=ml5Ugq7Qcfc.

“Fresh Build Friday—Clapton/24g Parallel Build”, retrieved online Apr. 7, 2017, from: https://www.youtube.com/watch?v=P1xFUnAUG1Y.

“Staged Heating Coil”, retrieved online Apr. 7, 2017, from: https://www.youtube.com/watch?v=CzxaTKO_Clo.

“Staged Heating Coil 0.08 ohm . . . Build with Caution”, retrieved online Apr. 7, 2017, from: https://www.youtube.com/watch?v=tQKxfqZG_cE.

“Staged Twisted Heating Coil Build Mutation X V2”, retrieved online Apr. 7, 2017, from: https://www.youtube.com/watch?v=HiaCuivUgAY.

“0.11 ohms Dual Staged Parallel coil building tutorial”, retrieved online Apr. 7, 2017, from: https://www.youtube.com/watch?v=yTqjAebyWQY.

“Transformer Coil: Tutorial Build for Clouds & Flavor”, retrieved online Apr. 7, 2017, from: https://www.youtube.com/watch?v=lcqG8zXPeQ0.

* cited by examiner

ELECTRONIC SMOKING DEVICE

PRIORITY CLAIM

This application claims priority to EP Patent Application No. 15159775.4, filed Mar. 19, 2015, and now pending.

FIELD OF INVENTION

The present invention relates generally to electronic smoking devices and in particular electronic cigarettes.

BACKGROUND OF THE INVENTION

An electronic smoking device, such as an electronic cigarette (e-cigarette), typically has a housing accommodating an electric power source (e.g. a single use or rechargeable battery, electrical plug, or other power source), and an electrically operable atomizer. The atomizer vaporizes or atomizes liquid supplied from a reservoir and provides vaporized or atomized liquid as an aerosol. Control electronics control the activation of the atomizer. In some electronic cigarettes, an airflow sensor is provided within the electronic smoking device which detects a user puffing on the device (e.g., by sensing an under-pressure or an air flow pattern through the device). The airflow sensor indicates or signals the puff to the control electronics to power up the device and generate vapor. In other e-cigarettes, a switch is used to power up the e-cigarette to generate a puff of vapour.

SUMMARY OF THE INVENTION

In one aspect an atomizer for an electronic smoking device is provided which comprises at least a first heating wire and a second heating wire. The first and second heating wires are wound together to form a common heating coil. Further, the first and second heating wires differ in at least one physical parameter resulting in different thermal properties of the first and second heating wire.

Different physical parameters of the first and second heating wires may relate to at least one of the following non-exclusive list of physical parameters of the heating wires: material; structure; wire locations or winding axes location within the common heating coil; wire diameter, diameters of a turn of the first and second heating wires; sizes and structures of cross sectional areas, surface profiles, length, and others.

Further provided is an electronic smoking device with the inventive atomizer.

The characteristics, features and advantages of this invention and the manner in which they are obtained as described above, will become more apparent and be more clearly understood in connection with the following description of exemplary embodiments, which are explained with reference to the accompanying drawings.

BRIEF DESCRIPTION OF THE DRAWINGS

In the drawings, same element numbers indicate same elements in each of the views.

DESCRIPTION OF THE PREFERRED EMBODIMENTS

Figure 1:
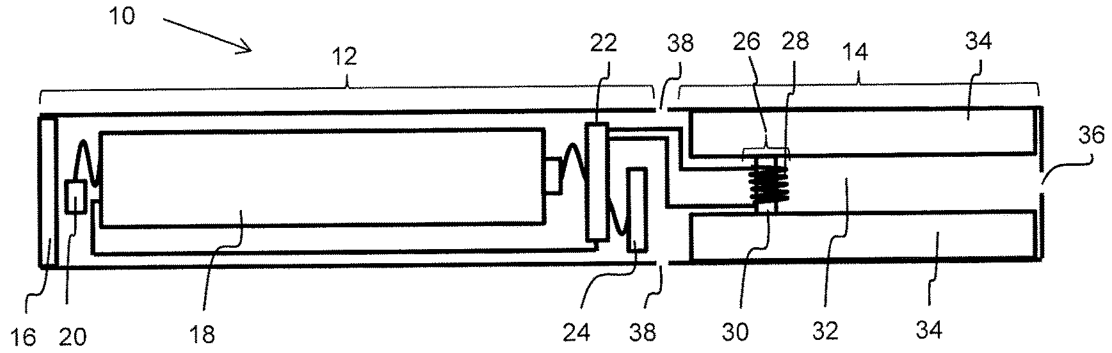
FIG. 1 is a schematic cross-sectional illustration of an exemplary e-cigarette.

Throughout the following, an electronic smoking device will be exemplarily described with reference to an e-cigarette. As is shown in FIG. 1, an e-cigarette 10 typically has a housing comprising a cylindrical hollow tube having an end cap 16. The cylindrical hollow tube may be single piece or a multiple piece tube. In FIG. 1, the cylindrical hollow tube is shown as a two piece structure having a battery portion 12 and an atomizer/liquid reservoir portion 14. Together the battery portion 12 and the atomizer/liquid reservoir portion 14 form a cylindrical tube which is approximately the same size and shape as a conventional cigarette, typically about 100 mm with a 7.5 mm diameter, although lengths may range from 70 to 150 or 180 mm, and diameters from 5 to 20 mm.

The battery portion 12 and atomizer/liquid reservoir portion 14 are typically made of steel or hardwearing plastic and act together with the end cap 16 to provide a housing to contain the components of the e-cigarette 10. The battery portion 12 and an atomizer/liquid reservoir portion 14 may be configured to fit together by a friction push fit, a snap fit, or a bayonet attachment, magnetic fit, or screw threads. The end cap 16 is provided at the front end of the battery portion 12. The end cap 16 may be made from translucent plastic or other translucent material to allow an LED 20 positioned near the end cap to emit light through the end cap. The end cap can be made of metal or other materials that do not allow light to pass.

An air inlet may be provided in the end cap, at the edge of the inlet next to the cylindrical hollow tube, anywhere along the length of the cylindrical hollow tube, or at the connection of the battery portion 12 and the atomizer/liquid reservoir portion 14. FIG. 1 shows a pair of air inlets 38 provided at the intersection between the battery portion 12 and the atomizer/liquid reservoir portion 14.

A battery 18, a light emitting diode (LED) 20, control electronics 22 and optionally an airflow sensor 24 are provided within the cylindrical hollow tube battery portion 12. The battery 18 is electrically connected to the control electronics 22, which are electrically connected to the LED 20 and the airflow sensor 24. In this example the LED 20 is at the front end of the battery portion 12, adjacent to the end cap 16 and the control electronics 22 and airflow sensor 24 are provided in the central cavity at the other end of the battery 18 adjacent the atomizer/liquid reservoir portion 14.

The airflow sensor 24 acts as a puff detector, detecting a user puffing or sucking on the atomizer/liquid reservoir portion 14 of the e-cigarette 10. The airflow sensor 24 can be any suitable sensor for detecting changes in airflow or air pressure such a microphone switch including a deformable membrane which is caused to move by variations in air pressure. Alternatively the sensor may be a Hall element or an electro-mechanical sensor.

The control electronics 22 are also connected to an atomizer 26. In the example shown, the atomizer 26 includes a heating coil 28 which is wrapped around a wick 30 extending across a central passage 32 of the atomizer/liquid reservoir portion 14. The coil 28 may be positioned anywhere in the atomizer 26 and may be transverse or parallel to the liquid reservoir 34. The wick 30 and heating coil 28 do not completely block the central passage 32. Rather an air gap is provided on either side of the heating coil 28 enabling air to flow past the heating coil 28 and the wick 30. The atomizer may alternatively use other forms of heating elements, such as ceramic heaters, or fiber or mesh material heaters. Nonresistance heating elements such as sonic, piezo and jet spray may also be used in the atomizer in place of the heating coil.

The central passage 32 is surrounded by a cylindrical liquid reservoir 34 with the ends of the wick 30 abutting or extending into the liquid reservoir 34. The wick 30 may be a porous material such as a bundle of fiberglass fibers, with liquid in the liquid reservoir 34 drawn by capillary action from the ends of the wick 30 towards the central portion of the wick 30 encircled by the heating coil 28.

The liquid reservoir 34 may alternatively include wadding soaked in liquid which encircles the central passage 32 with the ends of the wick 30 abutting the wadding. In other embodiments the liquid reservoir 34 may comprise a toroidal cavity arranged to be filled with liquid and with the ends of the wick 30 extending into the toroidal cavity.

An air inhalation port 36 is provided at the back end of the atomizer/liquid reservoir portion 14 remote from the end cap 16. The inhalation port 36 may be formed from the cylindrical hollow tube atomizer/liquid reservoir portion 14 or maybe formed in an end cap.

In use, a user sucks on the e-cigarette 10. This causes air to be drawn into the e-cigarette 10 via one or more air inlets, such as air inlets 38 and to be drawn through the central passage 32 towards the air inhalation port 36. The change in air pressure which arises is detected by the airflow sensor 24 which generates an electrical signal that is passed to the control electronics 22. In response to the signal, the control electronics 22 activate the heating coil 28 which causes liquid present in the wick 30 to be vaporized creating an aerosol (which may comprise gaseous and liquid components) within the central passage 32. As the user continues to suck on the e-cigarette 10, this aerosol is drawn through the central passage 32 and inhaled by the user. At the same time the control electronics 22 also activate the LED 20 causing the LED 20 to light up which is visible via the translucent end cap 16 mimicking the appearance of a glowing ember at the end of a conventional cigarette. As liquid present in the wick 30 is converted into an aerosol more liquid is drawn into the wick 30 from the liquid reservoir 34 by capillary action and thus is available to be converted into an aerosol through subsequent activation of the heating coil 28.

Some e-cigarette are intended to be disposable and the electric power in the battery 18 is intended to be sufficient to vaporize the liquid contained within the liquid reservoir 34 after which the e-cigarette 10 is thrown away. In other embodiments the battery 18 is rechargeable and the liquid reservoir 34 is refillable. In the cases where the liquid reservoir 34 is a toroidal cavity, this may be achieved by refilling the liquid reservoir 34 via a refill port. In other embodiments the atomizer/liquid reservoir portion 14 of the e-cigarette 10 is detachable from the battery portion 12 and a new atomizer/liquid reservoir portion 14 can be fitted with a new liquid reservoir 34 thereby replenishing the supply of liquid. In some cases, replacing the liquid reservoir 34 may involve replacement of the heating coil 28 and the wick 30 along with the replacement of the liquid reservoir 34. A replaceable unit comprising the atomizer 26 and the liquid reservoir 34 is called a cartomizer.

The new liquid reservoir 34 may be in the form of a cartridge having a central passage 32 through which a user inhales aerosol. In other embodiments, aerosol may flow around the exterior of the cartridge 32 to an air inhalation port 36.

Of course, in addition to the above description of the structure and function of a typical e-cigarette 10, variations also exist. For example, the LED 20 may be omitted. The airflow sensor 24 may be placed adjacent the end cap 16 rather than in the middle of the e-cigarette. The airflow sensor 24 may be replaced with a switch which enables a user to activate the e-cigarette manually rather than in response to the detection of a change in air flow or air pressure.

Different types of atomizers may be used. Thus for example, the atomizer may have a heating coil in a cavity in the interior of a porous body soaked in liquid. In this design aerosol is generated by evaporating the liquid within the porous body either by activation of the coil heating the porous body or alternatively by the heated air passing over or through the porous body. Alternatively the atomizer may use a piezoelectric atomizer to create an aerosol either in combination or in the absence of a heater.

Figure 2:
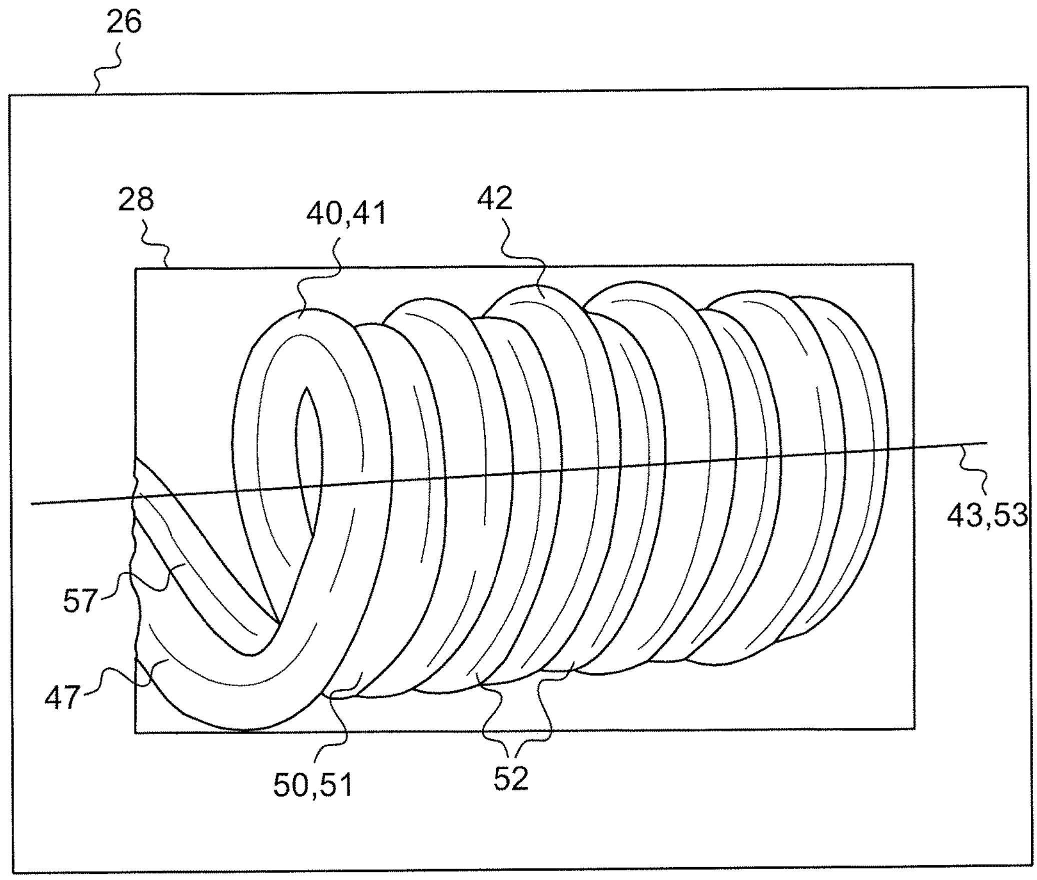
FIG. 2 is a schematic view of an atomizer in a first embodiment.
Figure 3:
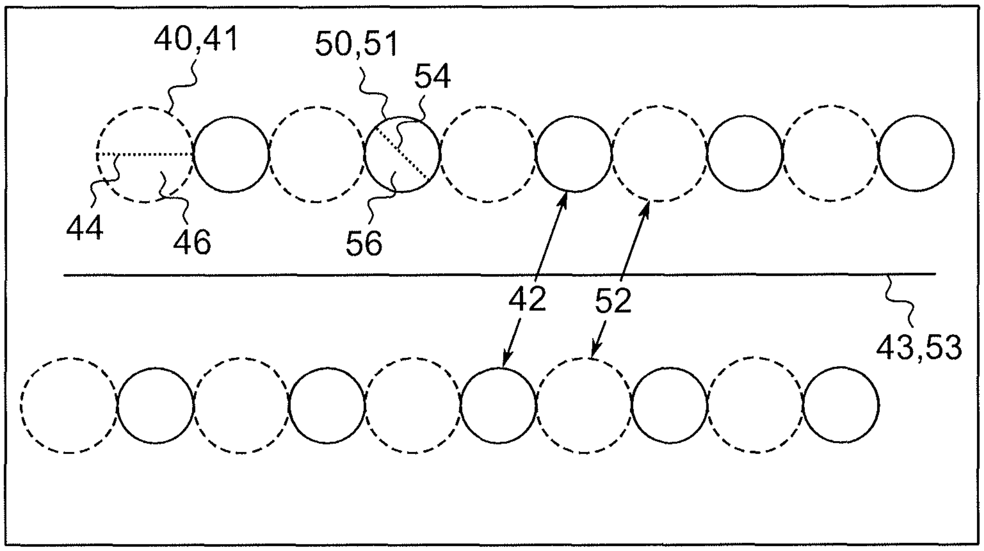
FIG. 3 is a section view through the atomizer of FIG. 2.

FIG. 2 shows a schematic view of an atomizer 26 in a first embodiment. FIG. 3 shows a cut through the inventive atomizer 26 of FIG. 2 in a plane going through a center or winding axis 43, 53 of the first and second heating wires 40, 50. The atomizer 26 as shown in FIG. 2 can be incorporated into the e-cigarette 10 of FIG. 1 or other e-cigarettes which employ an atomizer 26. An atomizer 26 atomizes or vaporizes the liquid stored in the e-cigarette 10 of FIG. 1. The atomizer 26 in the embodiment shown in FIG. 2 includes a heating coil 28. The heating coil 28 comprises at least a first heating wire 40 and a second heating wire 50. The first and second heating wires 40, 50 are wound together to form the common heating coil 28. The first and second heating wires 40, 50 are parallel to each other. Each of the heating wires 40, 50 which constitute the common heating coil 28 are wound to form a first heating coil 41 and a second heating coil 51, respectively. Each loop of a heating wire 40, 50 is in the following named a turn 42, 52. In FIG. 2, the first and second heating coils 41, 51 extend from left to right with a horizontal center or winding axis 43, 53. The first heating wire 40 has two end portions 47 (one on the left, shown in FIG. 2; one on the right, not shown) which are used to electrically contact the first heating wire 40. Similarly, the second heating wire 50 has two end portions 57 which are used to electrically contact the second heating wire 50. The first and second heating wires 40, 50 are electrically contacted in parallel.

As can be seen from FIG. 2, the first and second heating coils 41, 51 extend in the same direction and are staggered along the winding or center axis 43, 53 with respect to each other such that one turn 42 of the first heating wire 40 is neighbored by a turn 52 of the second heating wire 50. In the center region of the heating coil 28, the one turn 42 of the first heating wire 40 is neighbored by two turns 52 of the second heating wire 50. The two heating coils 41, 51 are wound together to form a single or common heating coil 28.

In other words, the first and second heating coils 41, 51 are displaced along the center axis 43, 53 with an offset such that at least one turn 42 of the first heating coil 41 is placed between two turns 52 of the second heating coil 51, vice versa. The center axis 43 of the first heating coil 41 is identical to a center axis 53 of the second heating coil 51. A turn 42 of the first heating wire 40 directly contacts two turns 52 of the second heating wire 50. This allows the heating coil 28 to heat up quickly and to reduce a delay until an aerosol is produced from the liquid.

The first and second heating wires 40, 50, or the first and second heating coils 41, 51 according to all embodiments of the invention have at least one different physical parameter resulting in different thermal properties of the heating wires 40, 50 and heating coils 41, 51. In the embodiment shown in FIG. 2 and FIG. 3, the diameter 44 of the first heating wire 40 is greater than the diameter 54 of the second heating wire 50. Both heating wires 40, 50 are solid wires with constant cross section 46, 56 and planar outer surfaces. Due to the different physical parameters, here different wire thicknesses, the first and second heating wires 40, 50 heat differently. The first and second heating wires 40, 50 have different heating profiles or heat transfer characteristics and heat up and cool down at different speeds. Thin wires like the second heating wire 50 heat up and cool down very fast reducing the delay until an aerosol is produced by the atomizer 26 in contact with a liquid of an e-cigarette 10. Also, thin wires generally reach a maximum temperature faster while thick wires take longer to heat up but also retain their heat for longer.

The combination of at least two heating wires 40, 50 having different physical parameters provides in comparison with a heating coil consisting of a single heating wire a more complex heat transfer characteristic of an atomizer 26 in an e-cigarette 10 and thus a more complex aerosol generation upon contact with the liquid stored in the e-cigarette 10. The vaping experience may become more multidimensional using the different thermal properties of different heating wires 40, 50 combined into a common heating coil 28. In the state of the art, this has been achieved with staggered power delivery to a single wire, while according to an embodiment such electronics could be omitted or structured less complex resulting in a cheaper and simpler way to achieve a similar goal with improved performance outcomes of the atomizer 26 and consequently the e-cigarette 10.

By using two different heating wires 40, 50 with different thermal properties, e.g. by using two different heating wire thicknesses together in a single heating coil 28, the surface area of the heating coil 28 for liquid contact is greater in comparison with a heating coil 28 formed from a single heating wire. This improves an aerosol generation in an electronic smoking device 10 the inventive atomizer 26 is supplied to.

FIG. 3 shows the different diameters 44, 54 of the first and second heating wires 40, 50 resulting in different sizes of their cross-sectional areas 46, 56. The first heating wire 40 has a larger diameter 44 and thus a larger cross-sectional area 46 than the second heating wire 50. The thicker first heating wire 40 has a lower resistance and provides more heat than the second heating wire 50. The turns 42 of the first heating wire 40 directly contact the neighboring turns 52 of the second heating wire 50 resulting in a dense heat transfer characteristic of the common heating coil 28.

The first and second heating wires 40, 50 of the first embodiment shown in FIGS. 2 and 3 differ in a single physical parameter, its wire thickness. However, the invention is not limited thereto. The heating wires 40, 50 can differ in a physical parameter, like the structure or size of cross-sections, surface profiles, materials etc. Some examples will be described in the following embodiments. The different embodiments can also be combined together such that the heating wires 40, 50 differ in two, three or a larger number of physical parameters leading to a complex heating profile of the common heating coil 28.

For instance, the heating wires 40, 50 of FIG. 2 and FIG. 3 may also be formed of a different material. One heating wire 40, 50 may be formed of a metal, one of a ceramic. Or both may be formed of different metals. One heating wire 40, 50 may be formed of a compound material or alloy, the other may be formed of a single material. The group of possible heating wire materials may comprise, for example, nickel, chromium, iron, aluminum, copper and alloys thereof as well as ceramics. Different heating wire materials will lead to different thermal properties and heat characteristic of the different heating coils 41, 51 resulting in a complex heat transfer pattern of the common heating coil 28 formed thereof.

Figure 4:
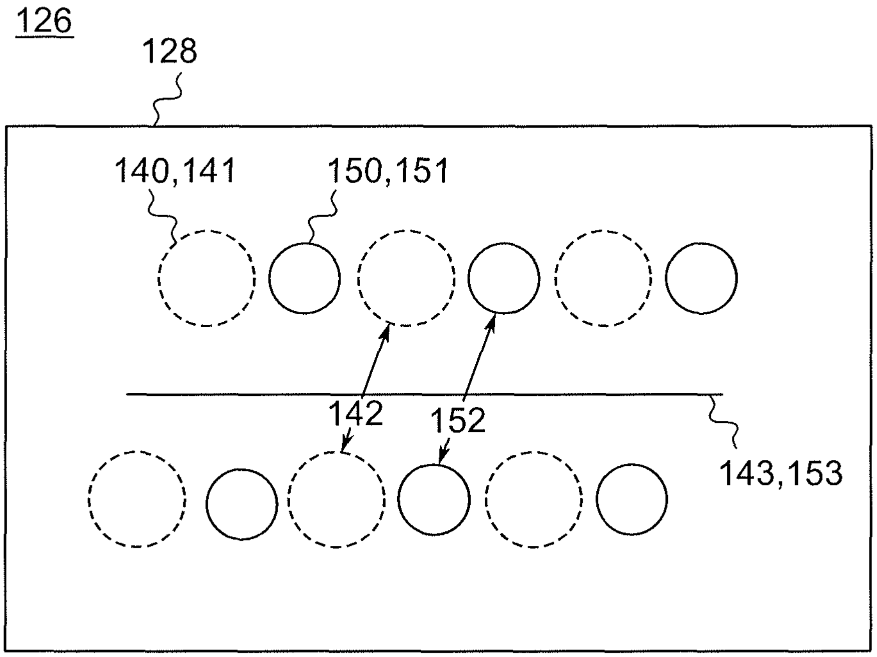
FIG. 4 is a section view through an atomizer in a second embodiment.

FIG. 4 is a vertical cut through an atomizer 126 with a common heating coil 128 in a second embodiment. The second embodiment differs from the first embodiment of FIGS. 2 and 3 in that the turns 142, 152 of first and second heating coils 141, 151 do not directly contact each other but are spaced apart from each other along the center axis 143, 153 of the heating coils 141, 151. Again, in a region spaced apart from the outer turns 142 of the heating coil 128, one turn 142 of the first heating wire 140 is neighbored by two turns 152 of the second heating wire 150, vice versa. Yet, the turns 142 of the first heating wire 140 and the turns 152 of the second heating wire 150 do not directly contact each other but are spaced apart from each other. This can be achieved by forming the first and second heating coils 41, 51 rigid, e.g. by use of a ceramic or metal material. Spacing apart the two heating coils 141, 151 results in a larger wire surface usable for liquid contact, but also results in a less dense heating profile of the common heating coil 128.

Figure 5:
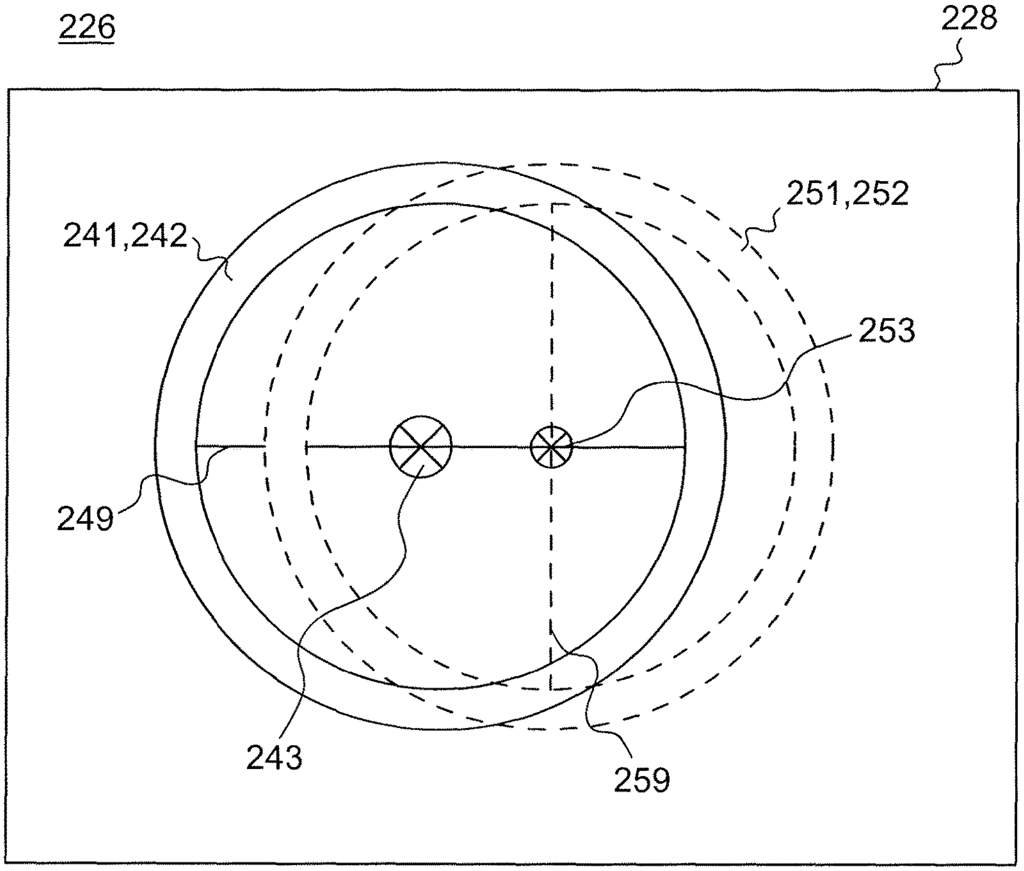
FIG. 5 is a view of a heating coil perpendicular to its winding axis in a third embodiment.

FIG. 5 is a cut through an atomizer 226 with a common heating coil 228 perpendicular to its winding axis in a third embodiment. Thus, the view is through the heating coil 228 along its length. Here, the first heating coil 241 and the second heating coil 251 have the same diameter 249, 259 of a turn 242, 252, but their center axes 243, 253 are displaced from each other. The displacement of the heating coils 241, 251 increases the complexity of the heating profiles of the common heating coil 228. However, the displacement of the heating coils 241, 251 with respect to each other alone does not result in a different thermal property of the first heating coil 241 with respect to the second heating coil 251. In order to have different thermal properties, they have to differ in an additional physical parameter. In the embodiment shown, the first and second heating coils 241, 251 are formed of different materials. A relative displacement of the second heating coil 251 may be limited such that the cross-sections of the turns 242, 252 of the first and second heating coils 241, 251 overlap. Preferably, the displacement of the center axis 253 of the second heating coil 251 from the center axis of the first heating coil 241 may be lower than a radius of a turn 42 of the first heating coil 241.

Figure 6:
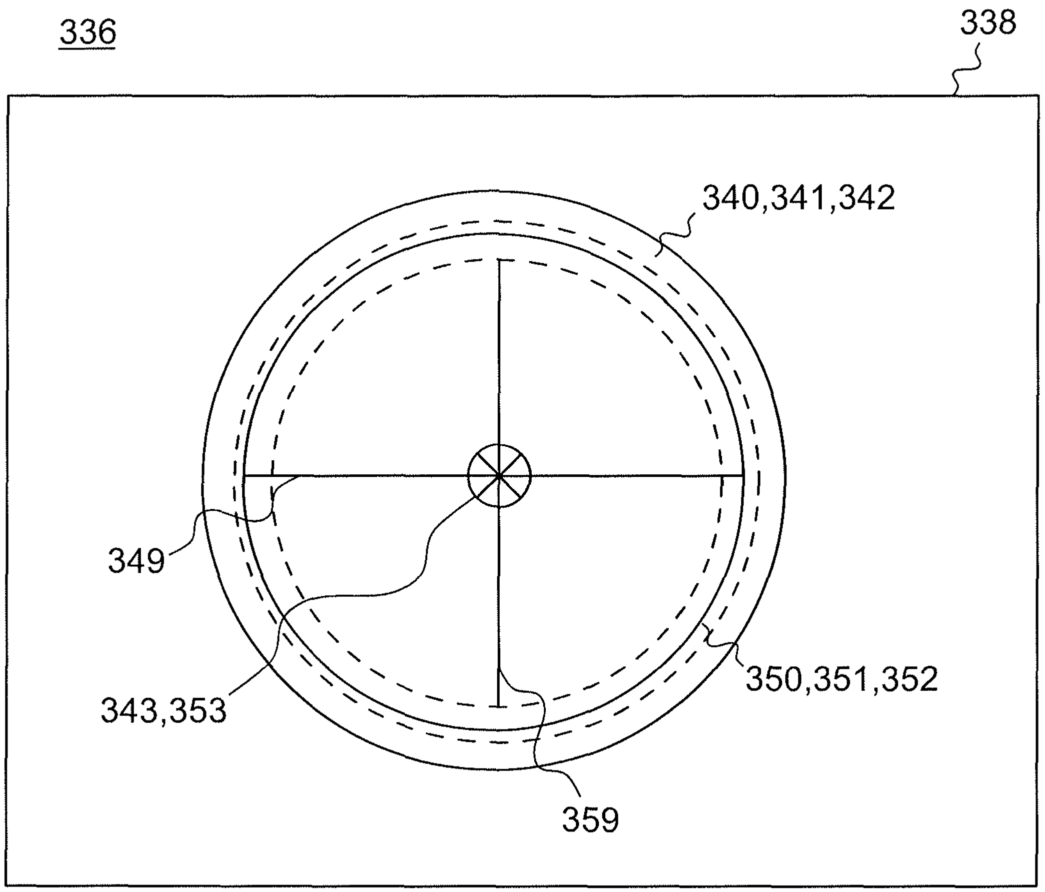
FIG. 6 is a view of a heating coil perpendicular to its winding axis in a fourth embodiment.

FIG. 6 is a view of an atomizer perpendicular to its winding axis in a fourth embodiment. In comparison to the third embodiment in FIG. 5, the heating coils 341, 351 have a common center axis 343, 353, but the diameter of a turn 342 of the first heating coil 341 is larger than the diameter of a turn 352 of the second heating coil 351. Thus, along the length of the common heating coil 328, its surface profile consists of valleys and peaks resulting in a complexity of a heat profile of the common heating coil 328. The two heating wires 340, 350 of this embodiment may have the same wire thicknesses but due to their different winding diameters 349, 359, the resulting heating coil 328 has a complex shape. In the preferred embodiment shown, the size of the winding diameter 359 of the second heating coil 351 is such that the cross-sections of the heating wires 340, 350 would still overlap in the cut shown in FIG. 6.

Figure 7:
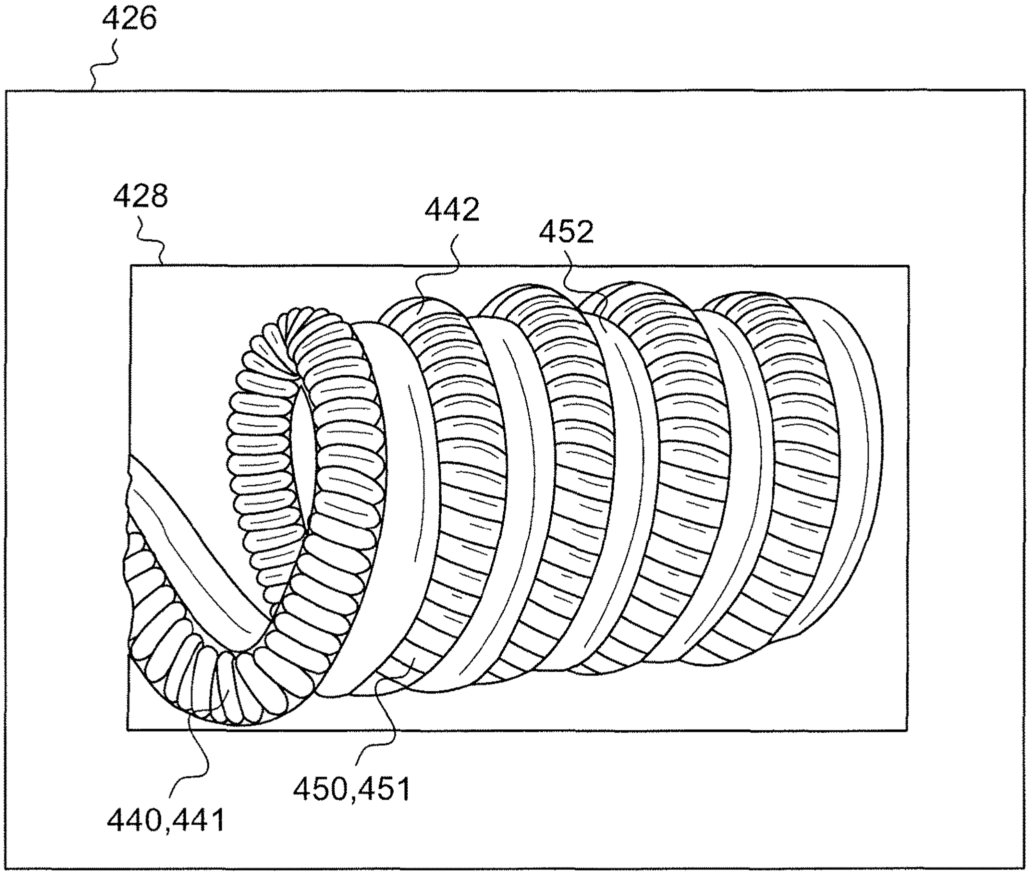
FIG. 7 is a schematic view of an atomizer in a fifth embodiment.

FIG. 7 is a schematic view of an atomizer 426 in a fifth embodiment. The fifth embodiment differs from the first embodiment in FIG. 2 in that the structure of the two heating wires 440, 450 differs. The first heating wire 440 is a twisted ribbon wire formed of a helix of spiral before it is wound to form the heating coil 428 together with second heating wire 450. Thus, the first heating wire 440 has a through-hole in its middle extending along its length and has varying cross sections 446 along its length. The second heating wire 450 is a solid wire with a non-varying circular cross-section 456 and a planar surface. Due to their different structure, the first and second heating wires 440, 450 shown in FIG. 2 have different surface profiles. The surface profile of the first heating wire 440 before being wound into a heating coil 441 consists of alternating valleys and peaks, whereas the surface profile of the second heating wire 450 is planar. The valleys of the first heating wire 440 increase the wire area usable for liquid contact and therefore improve the aerosol formation, while the solid second heating wire 450 provides more heat since it has a lower resistance than the first heating wire 440.

The examples of a ribbon heating wire 440 and a round heating wire 450 are not limiting. Any physical shape or structure of the heating wires 440, 450 can be envisaged, e.g. a stranded wire, an oval wire, a wire with a surface structure etc.

Figure 8:
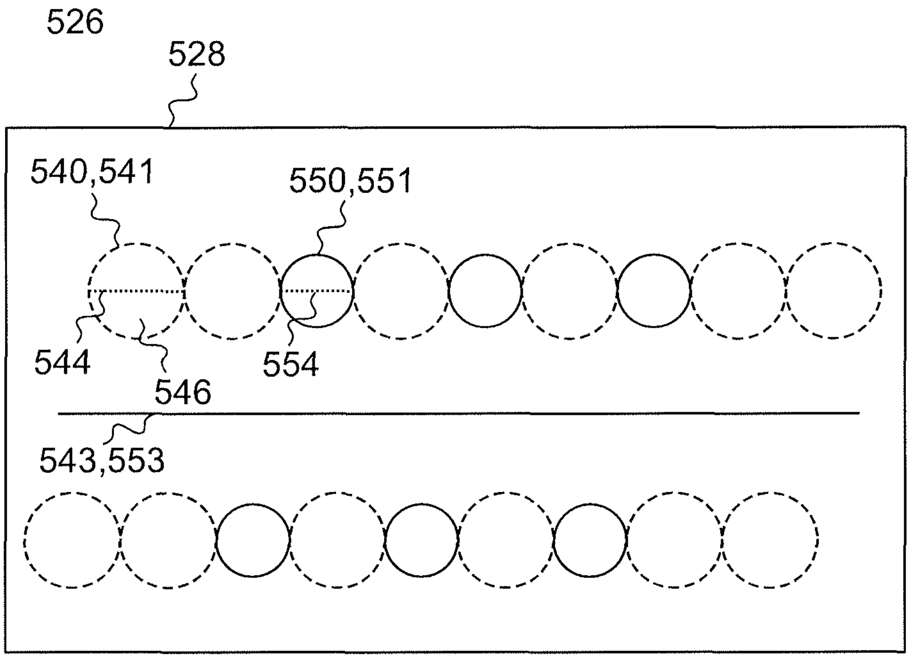
FIG. 8 is a vertical cut through an atomizer in a sixth embodiment.

FIG. 8 is a vertical cut through an atomizer 526 in a sixth embodiment. Here, the first and second heating wires 540, 550 have a different length and thus contribute with a different number of turns 542, 552 to the common heating coil 528. As exemplarily shown, while the first heating wire 540 contributes with six turns 542 to the common heating coil 528, the second heating wire 550 is shorter and contributes only with three turns 552 to the common heating coil 528.

Figure 9:
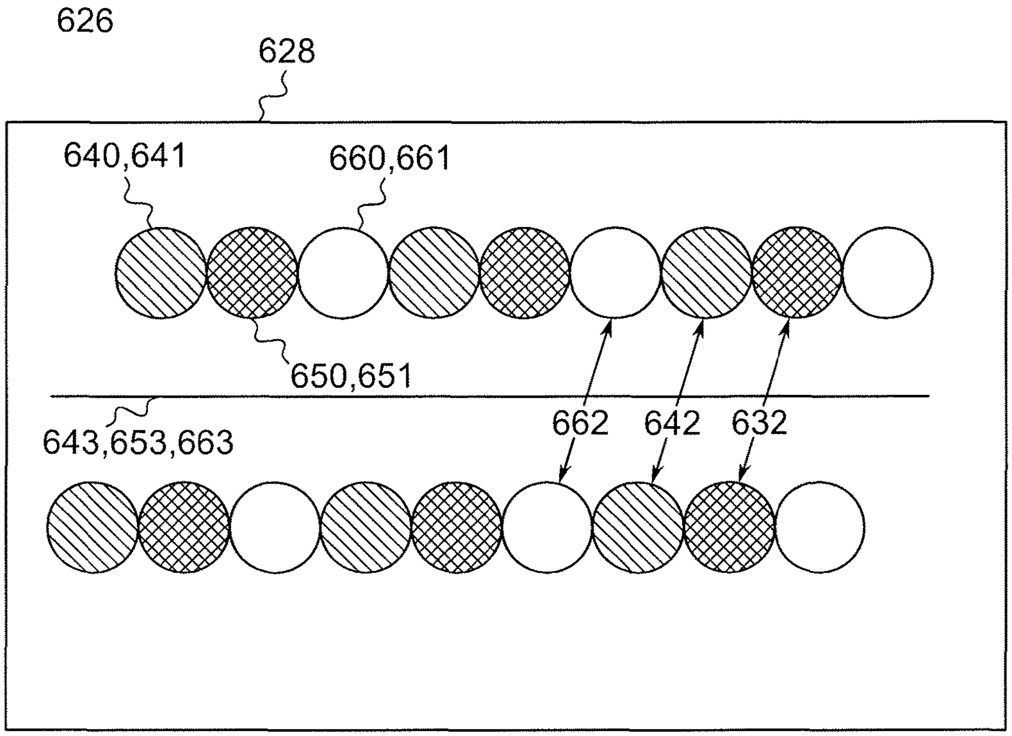
FIG. 9 shows a vertical cut through an atomizer in a seventh embodiment.

FIG. 9 shows a vertical cut through an atomizer 626 in a seventh embodiment. In this embodiment, a third heating wire 660 is additionally provided, wherein the first, second and third heating wires 640, 650, 660 are wound together to form the heating coil 628. One turn 642 of the first heating wire 640 contacts on one side a turn 652 of a second heating wire 650 and on the other side one turn 662 of the third heating wire 660. The first, second and third heating wires 640, 650, 660 in FIG. 9 are formed of different materials. While the first heating wire 640 is formed of a nickel-chromium alloy, the second heating wire 650 is formed of iron-chromium-aluminum alloy and the third heating wire 660 is formed of a nickel-iron alloy. Due to their different materials, the heating wires 640, 650, 660 have a different resistivity and therefore heat differently. Apart from their materials, the heating wires 640, 650, 660 do not differ in the embodiment shown. However, the third heating wire 660 could differ from the first and second heating wires 640, 650, respectively, also in any other physical parameter apart of its material.

Also more than three heating wires could be provided to form the common heating coil of the atomizer. Preferably, all least two of the group of heating wires differ in at least one physical parameter. In another embodiment, none of the provided heating wires would have an identical set of physical parameters as any other of the group of heating wires in the common heating coil.

Figure 10:
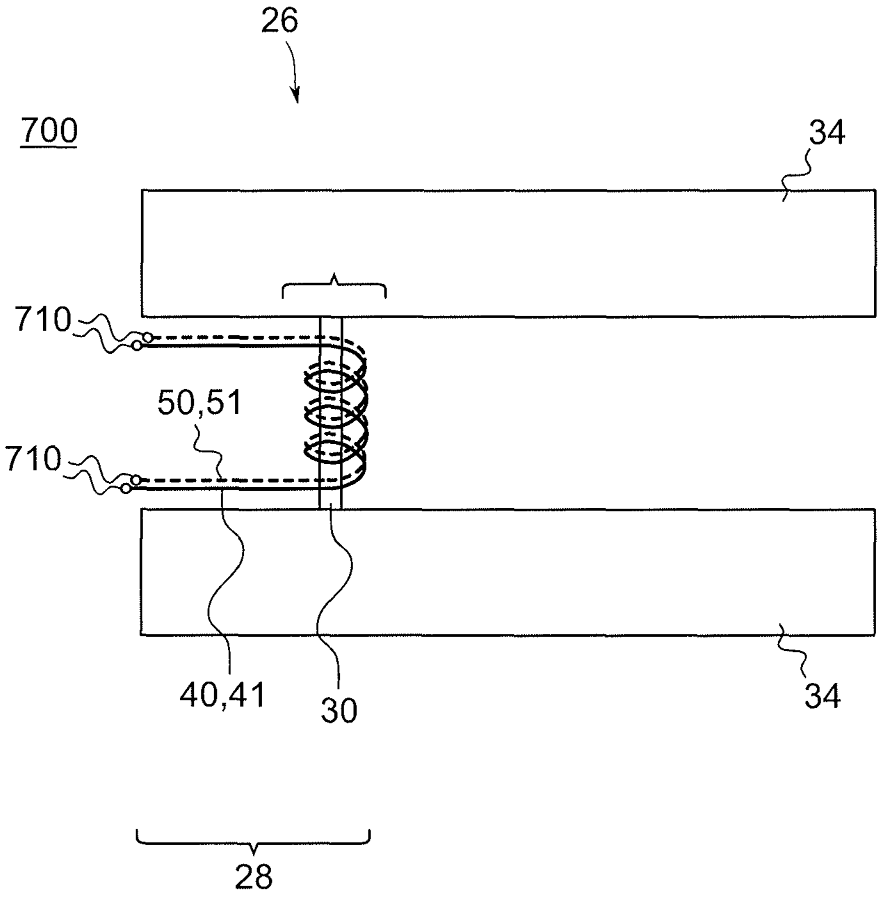
FIG. 10 shows a cartomizer with an atomizer in an eighth embodiment.

Electronic smoking devices may be structured such that the liquid reservoir can be removed from an electronic cigarette together with the atomizer and can be replaced by a new, refilled atomizer/liquid reservoir portion 14 being called a cartomizer. FIG. 10 shows a cartomizer 700 for an electronic smoking device 10 according to an embodiment. The cartomizer 700 comprises a liquid reservoir 34 as described in the context of FIG. 1 with an atomizer 26 of FIG. 2. However, all other embodiments of the atomizer described in the context of this invention may be used as an atomizer in FIG. 10. The atomizer/liquid reservoir portion 14 can be separated from the battery portion 12 and the cartomizer 700 can be removed and replaced. The first and second heating wires 40, 50, respectively the first and second heating coils 41, 51 of the atomizer 26 have electronic contacts 710, which upon fixation of the atomizer/liquid reservoir portion 14 to the battery portion 12 provide electrical contact to the battery 18. However, the electronic smoking device may be configured differently, for instance with an opening in its housing through which the cartomizer is removable or replaceable.

In summary, an atomizer for an electronic smoking device is provided comprising at least a first heating wire and a second heating wire. The first and second heating wires differ in at least one physical parameter and are wound together to form a common heating coil. Due to the at least one different physical parameter, the first and second heating wires have different thermal properties and heat differently. The first and second heating wires have different heating profiles or heat transfer characteristics. The first and second heating wires heat up and cool down at different speeds. In one aspect, a greater surface area for liquid contact may be provided. Different physical parameters of the first and second heating wires may relate to at least one of the following features:

the first and second heating wires are formed of a different material, the first and second heating wires have a different structure, the locations of the first and second heating wires within the common heating coil 28 differ, the diameter of the first and second heating wires differ, the diameters of a turn of the first and second heating wires differ, the first and second heating wires have different sizes or structures of cross sectional areas in a common cut through the heating coil, one of the first and second heating wires has a varying cross section while the other has a differently varying cross section or a constant cross section, the first and second heating wires have different surface profiles, surface treatments, or surface coatings, and the first and second heating wires have a different length.

Only one, a group of or all of the above features may be present in an embodiment of the invention.

Preferably, the first heating wire is wound into a first heating coil, the second heating wire is wound into a second heating coil, wherein the first and second coils extend in the same direction and are staggered along the winding axis with respect to each other such that one turn of the first heating wire is neighbored by at least one turn, preferably two turns of the second heating wire. The two heating coils are wound together to form a single heating coil. Preferably, the turns of the two heating coils are displaced along the winding axis with an offset such that one turn of the first heating coil is placed between two turns of the second heating coil, vice versa. Preferably, the center axis of the first heating coil is parallel to a center axis of the second heating coil. In one aspect, the center axis of the first heating coil is identical to a center axis of the second heating coil. This saves space and increases the heating performance of the heating coil.

In one aspect, a turn of the first heating wire directly contacts two turns of the second heating wire. This would allow the heating coil to heat up quickly and to reduce the delay until aerosol is produced. In one aspect, a diameter of the first heating wire is different from the diameter of the second heating wire. This may provide a simple way to achieve different heating profiles. In one aspect, the first heating wire and the second heating wire are made of different materials. In another aspect, a surface profile of the first heating wire is different from a surface profile of the second heating wire. Preferably, a cross section of a first heating wire varies differently along its length compared to a cross section of the second heating wire. A cross section of a first heating wire may vary along its length wherein the cross section of the second heating wire may be constant. In a vertical cut through the heating coil, a cross section of a first heating wire 40 may be different from a cross section of the second heating wire. For example, although wires having a round cross section are commonly available in various materials and diameters, one or more of the heating wires, or parts of it, may have a non-round cross section, such as a flatter ribbon-like wire.

The number of end portions of the heating coil is double the number of heating wires. Preferably, the first end portion of the first heating wire and the end portion of the second heating wire are coupled together into a first common contact portion and the second end portions of the first and second heating wires are coupled together into a second common contact portion, respectively.

In yet another embodiment, a third heating wire is additionally provided, wherein the first, second and third heating wires are wound together to form the heating coil. Preferably, one turn of the first heating wires contacts on one side one turn of a second heating wire and on the other side one turn of the third heating wire. The third heating wire differs from the first and/or second heating wire in at least one physical parameter, e.g. its material; its cross section; its variation of its cross section along its length; its length; and its surface profile such that the third heating wire has a different thermal property than the first and second heating wires.

In one embodiment, an electronic smoking device is provided comprising: a housing, a liquid reservoir provided inside the housing, and an atomizer as described above. The invention is not limited to a heating wire with a wick but may be used with any other element for providing the liquid to the heating wire.

While this invention has been described in connection with what is presently considered to be practical exemplary embodiments, it is to be understood that the invention is not limited to the disclosed embodiments, but, on the contrary, is intended to cover various modifications and equivalent arrangements included within the scope of the appended claims.

LIST OF REFERENCE SIGNS

10 e-cigarette
12 battery portion

14 atomizer/liquid reservoir portion
16 end cap
18 battery
20 light emitting diode (LED)
22 control electronics
24 airflow sensor
26 atomizer
28 heating coil
30 wick
32 central passage
34 liquid reservoir
36 air inhalation port
38 air inlets
40 first heating wire
41 first heating coil
42 turn of first heating wire
43 center axis of first heating wire
44 diameter of first heating wire
45 surface profile of first heating wire
46 cross section of first heating wire
47 first end portion of first heating wire
48 second end portion of first heating wire
49 diameter of turn of a first heating wire
50 second heating wire
51 second heating coil
52 turn of second heating wire
53 center axis of second heating wire
54 diameter of second heating wire
55 surface profile of second heating wire
56 cross section of second heating wire
57 first end portion of second heating wire
58 second end portion of second heating wire
59 diameter of turn of a second heating wire
660 third heating coil
662 turn of third heating wire
700 cartomizer
710 electrical contacts of heating wires

The invention claimed is:

1. An atomizer for an electronic smoking device comprising:

at least a first heating wire and a second heating wire wound together to form a common heating coil, and the first and second heating wires differing in at least one physical parameter resulting in the first and second heating wires having one or more different thermal properties; and the first heating wire is wound into a first heating coil, the second heating wire is wound into a second heating coil, the first and second heating coils extending in a first direction and staggered with respect to each other in the first direction such that one turn of the first heating wire is adjacent to at least one turn of the second heating wire.

2. The atomizer of claim 1 wherein a center axis of the first heating coil is parallel to a center axis of the second heating coil.

3. The atomizer of claim 1 wherein a center axis of the first heating coil is coaxial with a center axis of the second heating coil.

4. The atomizer of claim 1 wherein a diameter of the first heating wire is different from a diameter of the second heating wire.

5. An atomizer for an electronic smoking device comprising:

at least a first heating wire and a second heating wire wound together to form a common heating coil, the first and second heating wires differing in at least one physical parameter resulting in the first and second heating wires having one or more different thermal properties; and wherein a turn of the first heating wire directly contacts two turns of the second heating wire.

6. An atomizer for an electronic smoking device comprising:

at least a first heating wire and a second heating wire wound together to form a common heating coil, and the first and second heating wires differing in at least one physical parameter resulting in the first and second heating wires having one or more different thermal properties; and the first heating wire and the second heating wire are made of different materials.

7. An atomizer for an electronic smoking device comprising:

at least a first heating wire and a second heating wire wound together to form a common heating coil, the first and second heating wires differing in at least one physical parameter resulting the first and second heating wires having one or more different thermal properties; and a cross section of a first heating wire varies differently along its length than a cross section of the second heating wire.

8. The atomizer of claim 7 wherein the cross section of the first heating wire varies along its length and the cross section of the second heating wire is constant.

9. An atomizer for an electronic smoking device comprising:

at least a first heating wire and a second heating wire wound together to form a common heating coil, the first and second heating wires differing in at least one physical parameter resulting in the first and second heating wires having one or more different thermal properties; and wherein a cross section of the first heating wire is different from a cross section of the second heating wire.

10. An atomizer for an electronic smoking device comprising:

at least a first heating wire, a second heating wire, and a third heating wire wound together to form a common heating coil, the first, second and third heating wires differing from each other in at least one physical parameter resulting in the first, second and third heating wires having one or more different thermal properties.

11. A cartomizer for an electronic smoking device comprising:

a liquid reservoir and an atomizer in a cartridge housing, with the atomizer including:

at least a first heating wire and a second heating wire, the first and second heating wires wound together to form a common heating coil, the first and second heating wires differing in at least one physical parameter resulting in the first and second heating wires having one or more different thermal properties;

the first heating wire wound into a first heating coil, the second heating wire wound into a second heating coil, the first and second heating coils extending in a first direction and staggered with respect to each other in the first direction such that one turn of the first heating wire is adjacent to at least one turn of the second heating wire; and the atomizer is configured to atomize a liquid stored in the liquid reservoir.

12. An electronic smoking device comprising:

a housing;

a liquid reservoir and an atomizer in the housing with the atomizer including:

at least a first heating wire and a second heating wire wound together to form a common heating coil, the first and second heating wires differing in at least one physical parameter resulting in the first and second heating wires having one or more different thermal properties; and the first heating wire wound into a first heating coil, the second heating wire wound into a second heating coil, the first and second heating coils extending in a first direction and staggered with respect to each other in the first direction such that one turn of the first heating wire is adjacent to at least one turn of the second heating wire; and the atomizer is configured to atomize a liquid stored in the liquid reservoir.

* * * * *